United States Patent [19]
Phillips et al.

[11] Patent Number: 5,910,844
[45] Date of Patent: Jun. 8, 1999

[54] DYNAMIC THREE DIMENSIONAL VISION INSPECTION SYSTEM

[75] Inventors: Dennis D. Phillips; Brian H. Jones, both of Richardson, Tex.

[73] Assignee: Vistech Corporation, Richardson, Tex.

[21] Appl. No.: 08/892,869

[22] Filed: Jul. 15, 1997

[51] Int. Cl.$^6$ .................................................. G01B 11/24
[52] U.S. Cl. ...................... 356/375; 356/237.1; 356/394; 348/126
[58] Field of Search .................................. 356/237, 394, 356/375; 348/87, 126; 382/146, 145; 250/560, 561; 29/720, 721, 729, 740, 759

[56] References Cited

U.S. PATENT DOCUMENTS

| | | | |
|---|---|---|---|
| 5,140,643 | 8/1992 | Izumi et al. | 382/8 |
| 5,192,983 | 3/1993 | Tokura | 356/376 |
| 5,208,463 | 5/1993 | Honma et al. | 250/561 |
| 5,212,390 | 5/1993 | LeBeau et al. | 250/561 |
| 5,452,080 | 9/1995 | Tomiya | 356/237 |
| 5,528,371 | 6/1996 | Sato et al. | 356/372 |
| 5,563,703 | 10/1996 | Lebeau et al. | 356/237 |

FOREIGN PATENT DOCUMENTS 6-26835  2/1994  Japan .

*Primary Examiner*—Hoa Q. Pham
*Attorney, Agent, or Firm*—Mark W. Handley

[57] ABSTRACT

A vision inspection system is provided in which eight optical images are instantaneously recorded on singular image frames which are output from two optical cameras. An illumination source is provided for illuminating four spaced apart inspection regions which are disposed about an inspection window. Two optical signals of reflected light emanate from each of the four inspection regions and are directed toward two optical cameras, with the two optical signals from each of the optical regions being at different viewing angles and preferably from a single focal point. Optical directing members receive the optical signals from the various regions and direct the light to respective ones of the cameras. The optical directing members are selectively adjustable for accommodating components of various sizes. The optical inspection of each component instantaneously occurs by recording the eight optical images, on two frames, one frame being recorded by each of the cameras. Four of the optical signals from two of the inspection regions are paired for input into one of the optical cameras and recorded on a singular frame. Four of the optical signals from the other two of the inspection regions are paired for input into the other of the optical cameras. The components passing over the optical inspection window may be inspected on the fly, without requiring stoppage of each of the components thereabove.

19 Claims, 5 Drawing Sheets

DYNAMIC THREE DIMENSIONAL VISION INSPECTION SYSTEM

TECHNICAL FIELD OF THE INVENTION

The present invention relates in general to quality control inspection systems, and a particular to a vision system for providing three-dimensional inspection of electronic components.

BACKGROUND OF THE INVENTION

Prior art inspection systems have been provided for inspecting various components in quality control operations. In the manufacture of electronic components, optical inspection systems are often used to provide automated visual inspection of the packaging for electronic components. Various parameters are inspected such as whether the appropriate markings are correctly placed upon the component packages, whether the leads and the cases of the components are of the correct configuration, and whether the leads are manufactured and then formed in correct alignment. Lead alignment measurements include lead pitch, lead displacement, lead offset, lead span, lead standoff and lead coplanarity. High speed automatic inspection systems capable of high throughput are required to provide adequate quality control on an economic basis. As the complexity of electronic component packages have increased, the need for accurate automatic inspection systems has also increased.

One type of electronic component currently being manufactured in large volumes are quad flatpack components for flatpack assembly operations. Such quad flatpack components typically have a large number of leads that extend from all four sides of a rectangular or square shaped component package. Current lead spacings are approximately 0.016 inches. Components for surface mounting operations are typically inspected for lead alignment in order to assure the correct lead spacing and coplanarity between the lower surfaces of the leads which are directly mounted to surface mount circuit boards. Improper lead alignment may result in incorrect mounting of components to circuit boards, and lower production assembly yield rates.

Some prior art vision inspection systems have been provided for inspecting quad flatpack systems. Often, five to eight cameras are utilized for inspecting the components from various angles. When a large number of cameras are utilized for optical inspection purposes, each of the cameras has to be aligned and then corresponding images from various frames from the different cameras coordinated such that data may be processed for determining whether the lead alignment and packaging components are manufactured within acceptable limits. Further, prior art vision inspection systems typically stationarily position the components above a region proximate to the vision inspection system at which the various recording cameras are focused. However, having to stationarily position components above a particular position in relation to the vision inspection system requires stoppage of components thereabove and increases the time required for inspection.

SUMMARY OF THE INVENTION

The present invention disclosed and claimed herein comprises a vision inspection system in which eight optical images are instantaneously recorded on singular image frames which are output from two optical cameras. An illumination source is provided for illuminating four spaced apart inspection regions which are disposed about an inspection window. Two optical signals of reflected light emanate from each of the four inspection regions and are directed toward two optical cameras, with the two optical signals from each of the optical regions being at different viewing angles and preferably from a single focal point. Optical directing members receive the optical signals from the various regions and direct the light to respective ones of the cameras. The optical directing members are selectively adjustable for accommodating components of various sizes. The optical inspection of each component instantaneously occurs by recording the eight optical images, on two frames, one frame being recorded by each of the cameras. Four of the optical signals from two of the inspection regions are paired for input into one of the optical cameras and recorded on a singular frame. Four of the optical signals from the other two of the inspection regions are paired for input into the other of the optical cameras. The components passing over the optical inspection window may be inspected on the fly, without requiring stoppage of each of the components thereabove.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
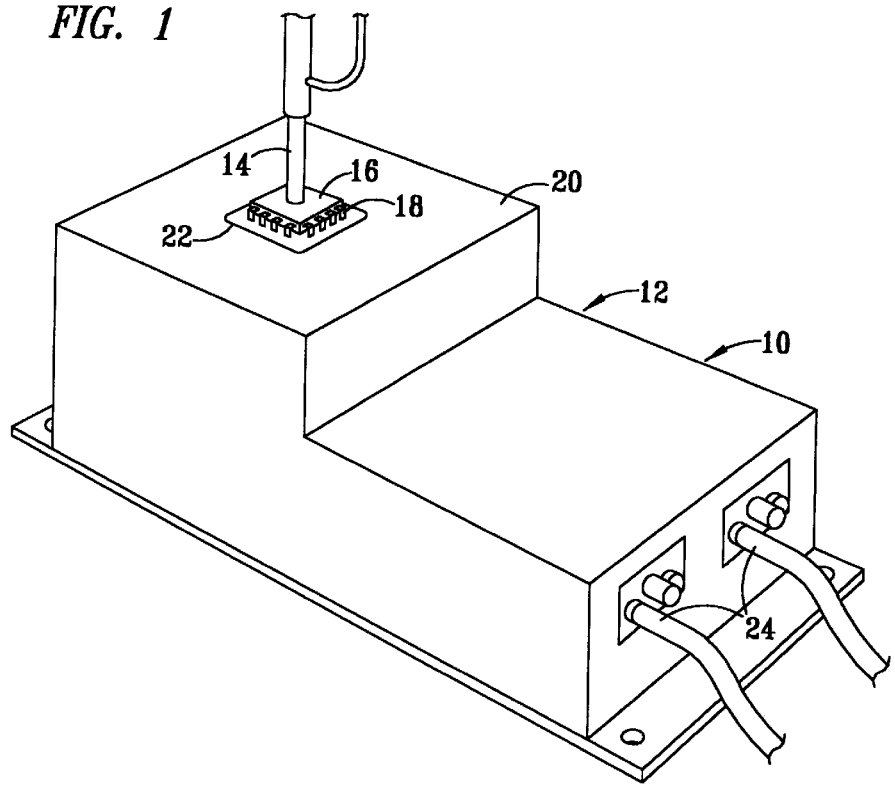
FIG. 1 illustrates perspective view of an optical unit of a vision inspection system made according to the present invention, with a transport member positioning an electronic component above an inspection window of the vision inspection system.

Referring now to FIG. 1, there is illustrated a vision inspection system 10 which is operable to inspect electronic components on the fly. The vision inspection system 10 has an optics unit 12. A transport member 14, which is depicted as a vacuum probe, is transporting an electronic component 16 having leads 18 above the optics unit 12. The optics unit 12 includes a housing 20 and an inspection window 22. As the electronic component 16, preferably a quad flatpack, is passed above the inspection window 22, the leads 18 on each of four sides of the electronic component 16 are simultaneously checked by a three-dimensional visual inspection of the placement of each of the leads 18. Electrical outputs 24 are provided for outputting electrical signals which represent various views of the leads 18 of the quad flatpack 16, such that a three-dimensional inspection of the electronic component 16 may be automatically provided by processing the output signals.

Figure 2:
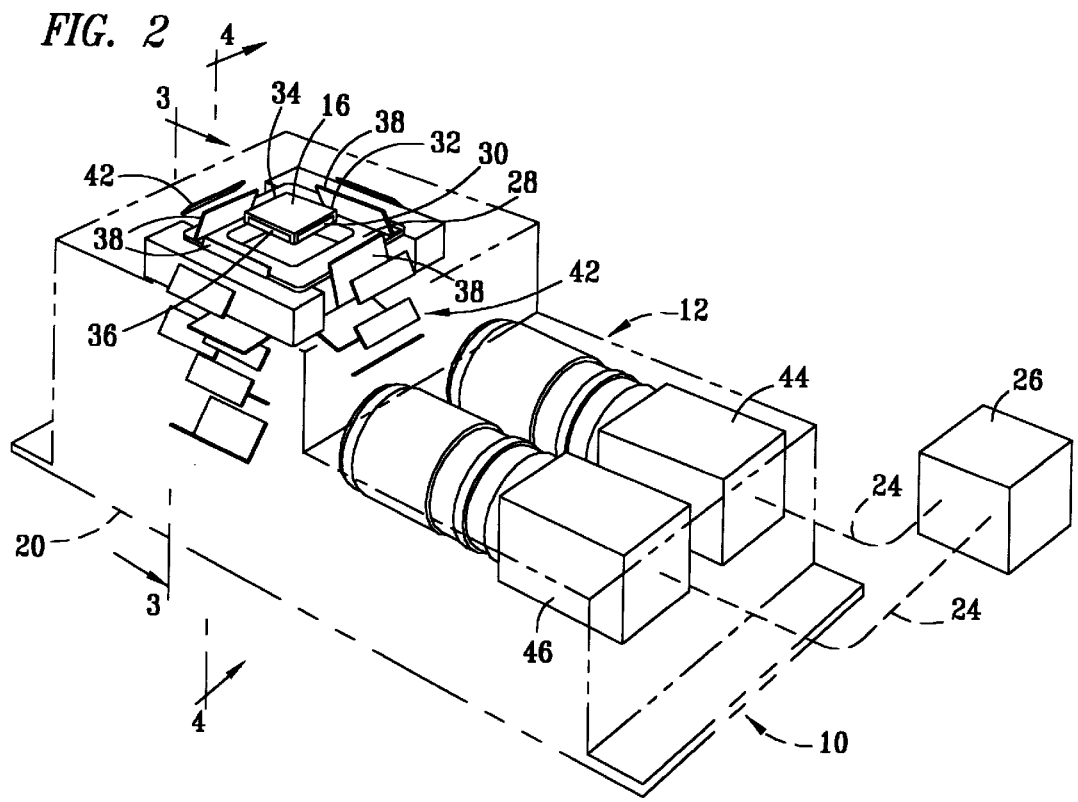
FIG. 2 illustrates a partial, cut-away view of the vision inspection system, with the exterior housing of the optical unit depicted in phantom and the interior components schematically depicted.

Referring now to FIG. 2, there is illustrated a schematic view of the vision inspection system 10, with the housing 20 of the optics unit 12 depicted in phantom. The vision inspection system 10 includes the optics unit 12 and a processor 26, which processes the output signals from the electrical outputs 24 to determine whether the leads and component packaging are properly aligned, and whether the leads 18 extend with the lowermost surfaces thereof in a singular plane for mounting in a surface mount assembly. The optics unit 12 of the vision inspection system 10 includes an illumination source 28. The illumination source 28 illuminates four regions 30, 32, 34 and 36 of the field of view of the optics unit 12. Four beam splitters 38 direct the illumination to shine upwardly toward the four regions 30, 32, 34 and 36. A beam splitter 40 (shown in FIG. 3) extends beneath the inspection window 22 and the illumination source 28 for illuminating the four regions 30, 32, 34 and 36 from below, but at a different angle of incidence than that at which the bean splitters 38 diffuse light upon the regions 30, 32, 34 and 36. The beam splitters 38 and 40 are preferably of a type made from glass coated by a dielectric material, and have a reflectivity of approximately 50% and a transmissivity of approximately 50%.

The optics unit 12 of the vision inspection system 10 further includes a plurality of light directing members 42, which are preferably provided by reflective surfaces. The light directing members 42 direct light from the four inspection regions 30–36 of the field of view into respective ones of the cameras 44 and 46. The cameras 44 and 46 provide optical signal translating devices, which translate the optical signals into corresponding electrical output signals. It should be noted that in the present invention reflective surfaces 42 provide the optical directing members, but in other embodiments of the present invention optical fibers may be used for directing the optical signals to the cameras 44 and 46. Preferably, the cameras 44 and 46 will instantaneously record the field of view of the regions 30–36, with regions 30 and 34 being recorded by the camera 44, and regions 32 and 36 being recorded by the camera 46. The electrical outputs 24 of the cameras 44 and 46 are then fed to the processor 26 for processing the optical signal to determine the various parameters regarding the placement of each of the leads 18 on all four sides of the electronic component 16. Further, processing provides information regarding whether the lowermost surfaces of the leads 18 are within a singular plane.

Figure 3:
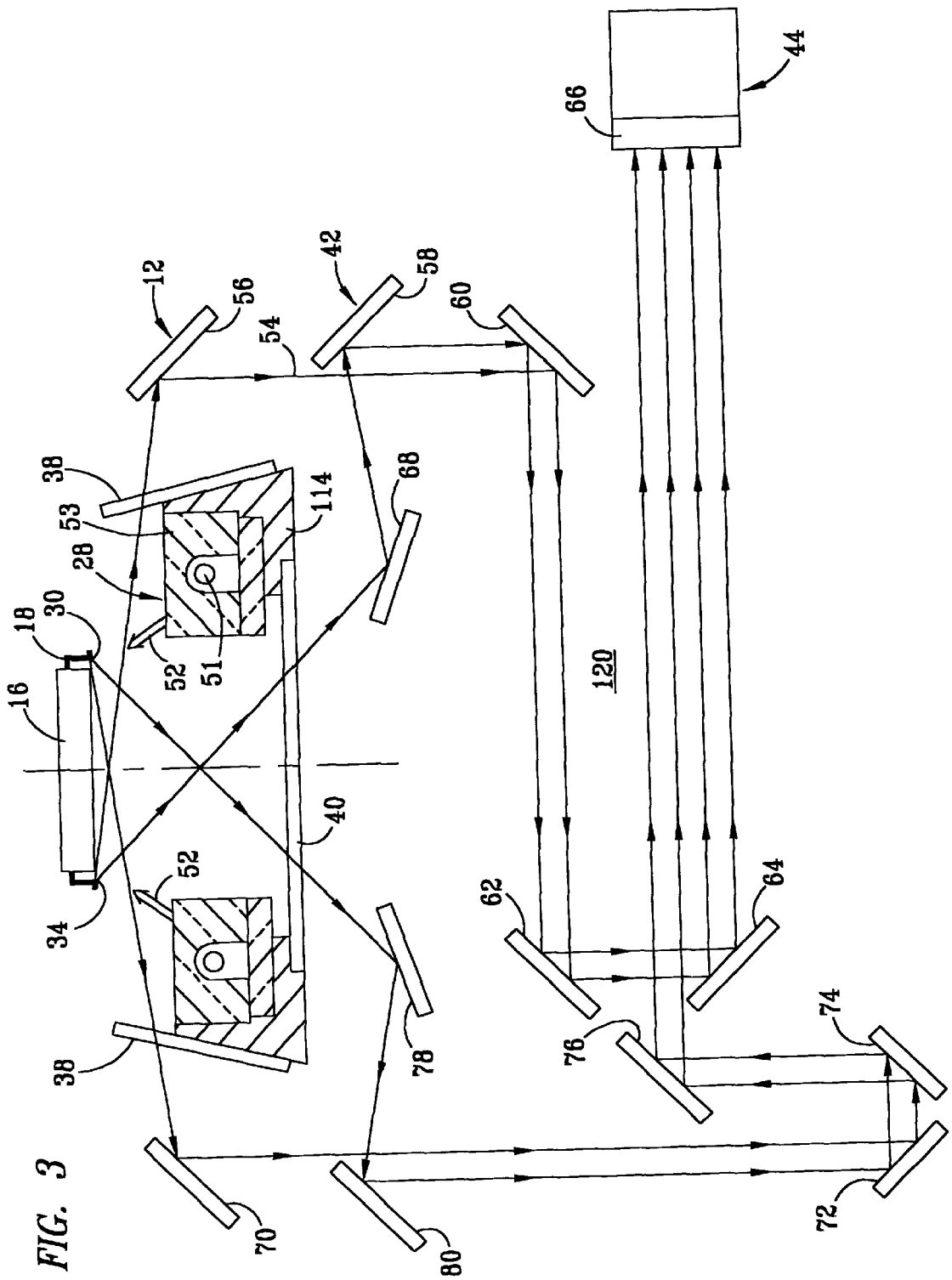
FIG. 3 illustrates a partial sectional view of the optical unit of the vision inspection system along section line 3—3 of FIG. 2, and schematically depicts a portion of the optical components of the optical unit.

Referring now to FIG. 3, there is illustrated a partial sectional view of the optics unit 12 of FIG. 2, which schematically depicts the optical components thereof. The illumination source 28 provides illumination 52 which illuminates the inspection regions 30 and 34. The illumination source 28 preferably includes a lamp 51 which is mounted within a translucent, square tubular structure 53 made of delrin which extends continuously around the lower side of the inspection window 22. The delrin block 53 in which the lamp 51 is located is translucent and diffuses the light emitted by the lamp 51. Preferably, the lamp 51 is a flash lamp which is strobed to illuminate the leads 18 of the component 16 as the component 16 is moving past the window 22. In other embodiments, light sources may be used for the lamp 51, such as those which continuously emit light for illumination, such as light emitting diodes, incandescent lamps and the like. Optical signals 54 then emit from the inspection regions 30 and 34, as light reflected from the lowermost surface of the leads 18, that is, from the surface of the leads 18 which are facing the inspection windows 22. The optical signals 54 are preferably reflected at different angular directions from the cut edges of the leads 18. The optical signals 54 extend downward, underneath the component 16, and are directed to the camera 44 by the plurality of reflective surfaces 42. It should be noted that the reflective surfaces 42 collectively provide optical signal directing members for directing the optical signals 54 into and ones of the cameras 44 and 46. Although reflective surfaces 42 are used in the present embodiment, in other embodiments other types of optical directing members may be used, such as optical fibers.

One of the optical signals 54 is then emitted from the region 34 and directed by reflective surfaces 56, 60, 62 and 64 into a lens 66 of the camera 44. A second one of the optical signals 54 is also emitted from the region 34 of the field of view of the optics unit 12 in a different direction, angularly displaced, from the one of the aforementioned optical signals, and is directed by optical surfaces 68, 58, 60, 62 and 64 to the lens 66 of the camera 44. These two optical signals are simultaneously emitted from the inspection region 34 of the field of view of the optics unit 12, preferably from a singular line of focus and in different directions, angularly displaced, from one another to provide two optical signals which may be processed to provide a three-dimensional inspection of the portion of the component 16 in the inspection region 34. A first of two optical signals from the inspection region 30 is directed by the reflective surfaces 70, 72, 74 and 76 to the lens 66 of the camera 44. The second of the two optical signals of different directions which is emitted from the inspection region 30 is directed by reflective surfaces 78, 80, 72, 74 and 76 to the lens 66 of the camera 44. Thus, four optical signals 54 are directed to the lens 66 to provide a two-directional view of t he region 30 and two-directional view of the region 34 such that four views are captured in a singular frame by the camera 44 at one instant in time.

Figure 4:
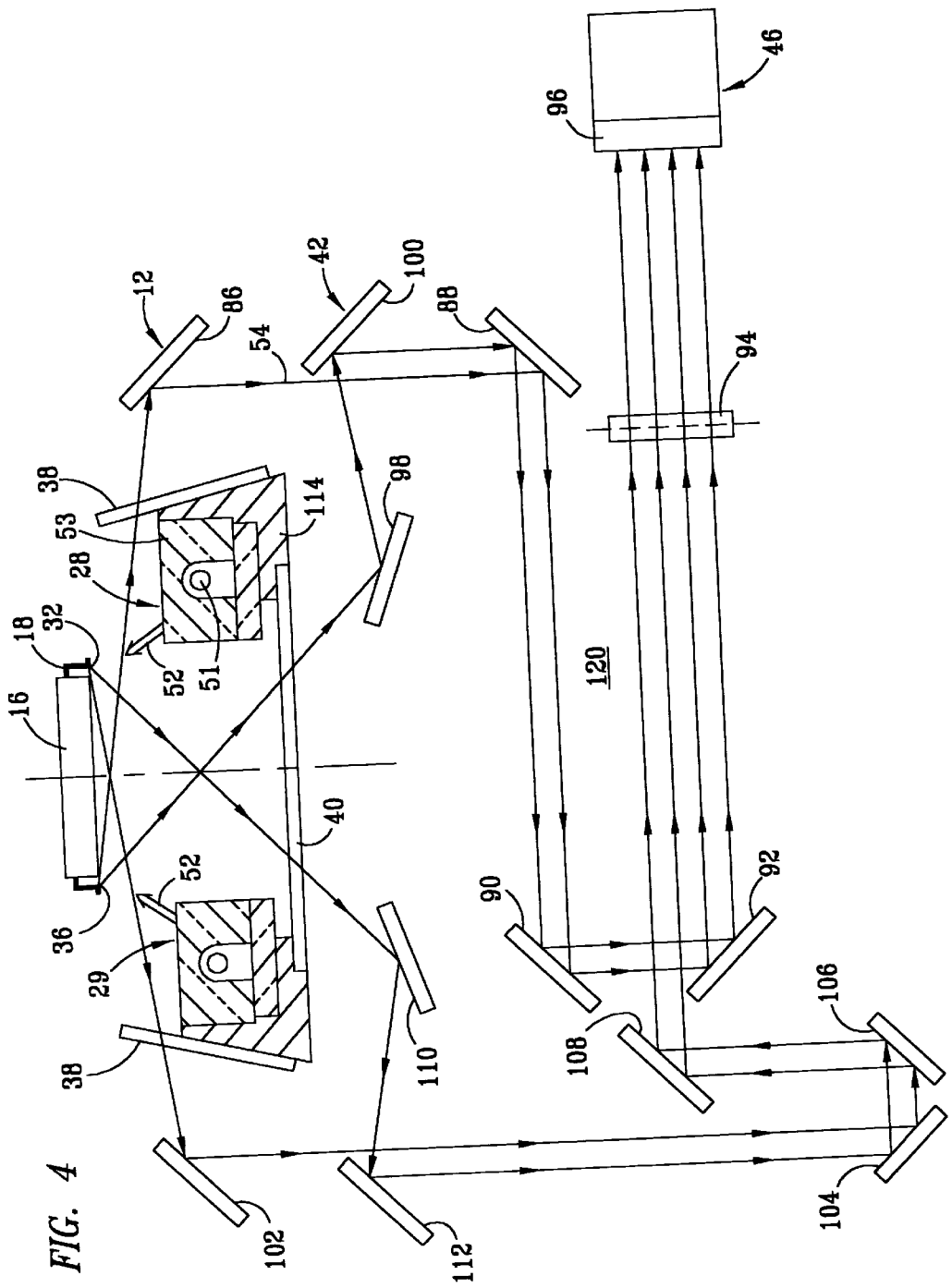
FIG. 4 illustrates a partial sectional view of the optical unit of the vision inspection system taken along section line 4—4 of FIG. 2, and schematically depicts a portion of the optical components of the optical unit.

Referring now to FIG. 4, there is illustrated a partial sectional view of the optics unit 12 taken along section line 4—4 of FIG. 2, which depicts the optical components thereof. The illumination source 28 provides illumination 52 which illuminates the regions 32 and 36 of the field of view to which the leads 18 of two opposite sides of the component 16 are passing. Optical signals 54 are then emitted from the regions 32 and 36 and are directed to the camera 46 by various ones of the reflective surfaces 42, which act as optical directing members. Two optical signals are emitted from the region 36 of the field of view of the optics unit 12, preferably from a singular line of focus on the edges of a portion of the leads 18. The first of the optical signals from the region 36 is directed by reflective surfaces 86, 88, 90, 92 and 94 to the lens 96 of the camera 46. It should be noted that the reflective surface 94 reflects a corresponding portion the optical signals 54 at a right angle to that at which it receives the corresponding optical signals, such that the cameras 44 and 46 depicted in FIG. 2 are arranged in a parallel alignment for receiving optical signals which are initially orthogonal to one another. This allows for viewing at two angles all four sides of a quad flatpack component, such as the electronic component 16 depicted in FIG. 1. The second optical signal from the region 36 is directed by the reflective surfaces 98, 100, 88, 90, 92 and 94 to the lens 96 of the camera 46.

Illumination 52 also causes optical signals 54 of reflected light to be emitted from the region 32 of the field of view of the optics unit 12 in two directions, preferably from a singular line of focus disposed along the edges of a portion of the leads 18. The optical signal 54 of the first direction emitted from the region 32 is directed by the reflective surfaces 102, 104, 106, 108 and 94 to the lens 96 of the camera 46. The optical signal of the second direction emitted from the region 32 is directed by the reflective surfaces 110, 112, 104, 106, 108 and 94 to the lens 96 of the camera 46. Thus, four optical signals representing two directions of view of the region 32 and two directions of view of the region 36 are recorded by the camera 46 in one frame, such that a three-dimensional analysis of the lowermost surfaces of the leads 18 and the component 16 may be analyzed by the processor 26, one in the region 32 and the other in the region 36 in a singular frame. A bracket 114 is provided for holding the beam splitters 38 and 40, and together with the beam splitters 38 and 40 prevents the illumination source 28 from directly passing light to various ones of the reflective surfaces/directing members 42. The beam splitters 38 and 40 reflect light from the illumination source 28 onto the leads 18.

Figure 5:
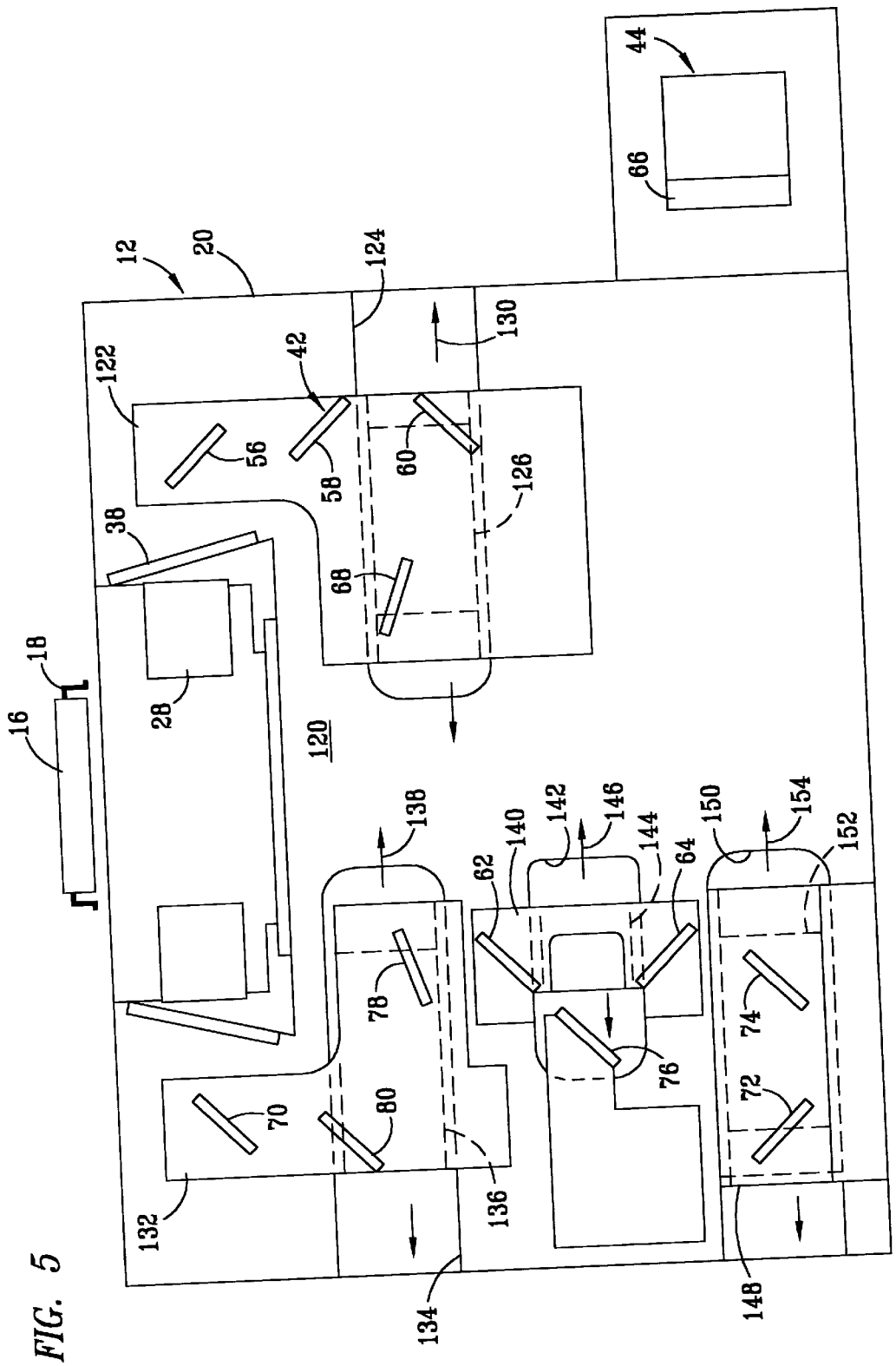
FIG. 5 illustrates a partial sectional view taken along section line 3—3 of FIG. 2, and schematically illustrates the mounting and adjustment mechanisms of reflective surfaces of the optical components of the optical unit of the vision inspection system.

Referring now to FIG. 5, there is illustrated a partial sectional view taken along section line 3—3 of FIG. 2, which illustrates the mounting and adjustment members of the reflective surfaces 42 of the optics unit 12. It should be noted that a sectional view taken along section line 4—4 of FIG. 2 would appear identical to that depicted in FIG. 5, with the exception of the addition of the reflective surface 94. That is, there are preferably four sides of the housing 20, which extend adjacent to the top and the bottom of the housing 20, and various ones of the reflective surfaces 42 mounted to respective ones of the four sides. The four sides are preferably orthogonal to adjacent ones of the four sides, and the reflective surfaces 42 are mounted to the four sides such that the surfaces 42 may be selectively adjustable for accommodating electronic components 16 of various sizes. A free space extends in a central region 120 of the housing 20 of the optical unit 12. Various ones of the optical signals 54 (shown in FIGS. 3 and 4) pass through the central region 120.

The reflective surfaces 56, 58, 60 and 68 are mounted to a carriage member 122. A groove 124 is formed into a sidewall of the housing 20 and is engaged by a slider member 126 to provide a linear bearing for moving the carriage 122 in a lineal direction 132. The slider member 126 is rigidly mounted to the carriage member 122, and slidably engages within the groove 124 to provide a linear bearing such that the carriage member 122 and the slider member 126 are moveable in the lineal direction 130.

The reflective surfaces 70, 80 and 78 are mounted to a carriage member 132. A groove 134 is formed into the sidewall of the housing 20. A slider 136 is mounted to the bottom of the carriage member 132 and slidably engages within the groove 134, such that the carriage member 132 and the slide member 136 are moveable in the lineal direction 138. The slider 136 engages within the groove 134 to provide a linear bearing.

The reflective surfaces 62 and 64 are mounted to the carriage member 140. A groove 142 is formed into the sidewall of the housing 20 for receiving a slider member 144 which is mounted to the carriage member 140. The slider member 144 slidable engages within the groove 142 such that the carriage member 140, the reflective surfaces 62 and 64 mounted thereto, and the slider member 144 move in the lineal direction 146. The groove 142 and the slider member 144 together provide a linear bearing.

The reflective surfaces 72 and 74 are mounted to a carriage member 148. A groove 150 is formed into the sidewall of the housing 20 for receiving a slider member 152, which is rigidly mounted to the carriage member 148. The groove 150 and the slider member 152 together operate in conjunction to provide a linear bearing such that the carriage member 148, the slider member 152, and the reflective surfaces 72 and 74 move in the lineal direction 154.

The reflective surface 76 is rigidly mounted to the sidewall of the housing 20. It does not move when the other of the reflective surfaces 42 are adjusted to accommodate components 16 of varying sizes. The lineal directions 130, 138, 146 and 154 are preferably parallel.

A sectional view taken along section line 4—4 of FIG. 2 will also result in carriage members which are identical to those depicted in FIG. 5, except for the addition of the reflective surface 94 for directing light received thereto at a right angle therefrom. The member 94 is also rigidly mounted to the housing 20, such that it will not move with respective ones of the carriage members, but it does have some alignment capability for initial calibration of the optics unit 12. It should be noted that once the cameras 44 and 46 are calibrated and the lenses 66 and 96 are focused, the optics unit 12 may be utilized for inspecting various ones of the components 16 of various sizes by adjusting carriage members 122, 132, 140 and 148, without requiring re-calibration of the cameras 44 and 46.

Figure 6:
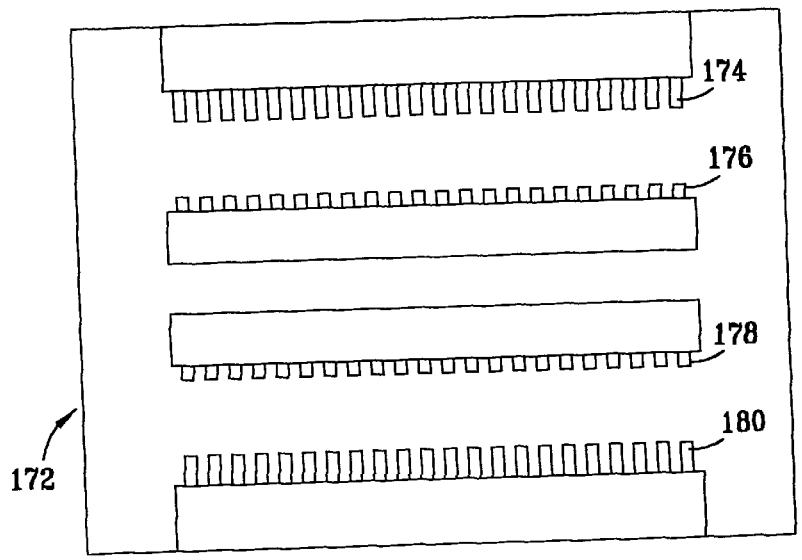
FIG. 6 illustrates a view of one of the frames output from one of the cameras of the von inspection system, with four views representing the four optical signals from two of the sides of the components being inspected being depicted thereon.

Referring now to FIG. 6, there is illustrated a view of one frame 172 provided from one of the electrical outputs 24 of one of the cameras 44 and 46. It should be noted that the four separate views 174, 176, 178 and 180 are provided in the single frame 172. The views 174 and 176 correspond to the images reflected from the two directions from the inspection region 30. The views 178 and 180 correspond to two views emitted in two directions from the inspection region 34. A frame from the other one of the cameras 44 and 46 would similarly depict four views, which each correspond to one of two directional views from the regions 32 and 36 which are orthogonally disposed to the regions 30 and 34 with respect to the positioning of the leads 18 of the component 16. Thus, a three-dimensional analysis may be provided of the positioning of each of the leads 18 on four separate sides of a component 16 by instantaneously recorded optical views of the inspection regions 30, 32, 34 and 36. This provides for on the fly viewing of a component 16 being passed beneath the window 22 of the optics unit 12.

Figure 7:
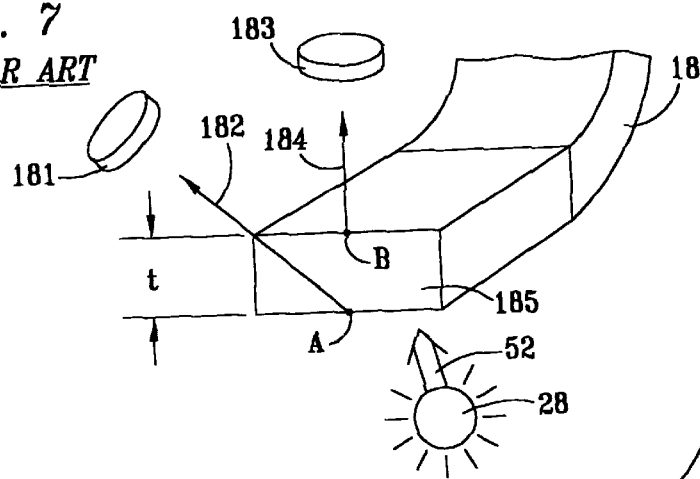
FIG. 7 illustrates a perspective view of one of the leads of a component being inspected by a prior art vision inspection system.

Referring now to FIG. 7, there is illustrated a lead of a component which is being inspected by a prior art inspection system which utilizes back-lighting. A light source 28 is providing illumination 52 which is directed upward from the light source 28 and onto the bottom of the lead 18. An optical signal 182 is passing adjacent to a point A located on an edge of the bottom of the lead 18 to a camera lens 181. An optical signal 184 is passing adjacent to a point B located on an edge of the top of the lead 18 and to a camera lens 183 located vertically above the point B on the top edge of the lead 18.

Light which is reflected is not passed upward as optical signals 182 and 184, but rather the light which does not impact the lead 18 is passed upward adjacent to the edges of the lead 18. The point B is separated from the point A by a thickness "t" of the lead 18. The shadow of the lead is analyzed by a processor to determine the location of the edges of the lead. Prior art inspection systems assume that the cut-end surface 185 of the lead 18 is vertical. However, this assumption gives rise to errors when the cut-end surface 185 of the lead 18 is not vertical, with points A and B on the edges adjacent to the end surface 185 not being vertically disposed one above another.

Figure 8:
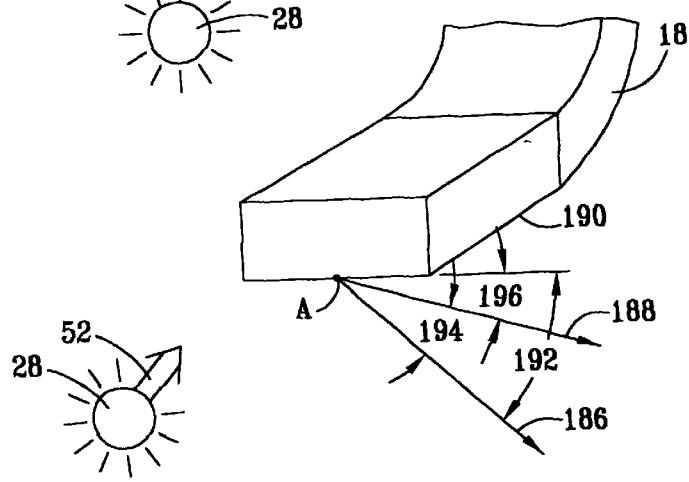
FIG. 8 illustrates a partial perspective view of one of the leads of a component being inspected by a vision inspection system made according to the present invention.

Referring now to FIG. 8, there is illustrated a perspective view of one of the leads 18 and two optical signals 186 and 188 from different directions of view from the lower side of the lead 18. The light source 28 is beneath the lead 18, and illumination 52 is reflected from the lower side 190 of the lead 18 to provide the two optical signals 186 and 188. The optical signals 186 and 188 are reflect off of the bottom of lead 18 from the point A at two different angular directions, which extend underneath the component 16 and into the central region 120 (shown in FIG. 5) of the optical unit 12, beneath the inspection window 22 (shown in FIG. 1). The point A represents a line of focus alone one side of the leads 18 of a component. The optical signal 186 is at 50 degree angle 192 from the horizontal. The optical signal 188 is at a 10 degree angle 196 from the horizontal, such that the optical signal 186 is angularly disposed from the optical signal 188 by a 40 degree angle 194. With the present invention, both of the optical signals 186 and 188 preferably focus on a singular focal point A, which extends as a line of focus on one side of the leads 18 of the component 16. The focal point A is located at an edge at the interface of the cut end and the lower side 190 of the lead 18. Thus, both of the optical signals 186 and 188 are from the same point A and the same edge of the lead 18, neither of the optical signals 186 and 188 are vertical such that the direction of each of the optical signals 186 and 188 has a horizontal component, and the optical signals 186 and 188 emanate from the same edge in two different angular directions such that a 3-dimensional determination of the location the edge of the lead 18 may be made. It should be noted that the most important parameter in determining the positions of various leads 18 of the component 16 for surface mount applications is whether the lower sides 190 of each of the leads 18 are in parallel alignment, within in a singular plane. The position of a single edge of each the leads 18 may be directly determined, even when the cut end of the leads 18 defining the edges are canted and not squared, by the two optical signals of different angles which emanate from each of such edges of the leads 18.

The present invention provides several advantages over prior art vision inspection systems. A component may be passed above the vision inspection system of the present invention, such as a quad flatpack component, and the positioning of the leads on all four sides of the component may be instantaneously determined by simultaneously recording the optical images of various inspection regions. The optical images comprise eight separate views, two of each side from different directions of view such that a three-dimensional image processing may occur for each side. Two optical cameras are utilized, with four views included in each frame from each of the cameras. Further, the optical views of each side may share a common focal point, rather than having the focal point separated by the thickness of the leads. The views are preferably provided by reflecting light off the bottom sides of the leads of the component, which face the viewing window of the optical inspection system.

Although the preferred embodiment has been described in detail, it should be understood that various changes, substitutions and alterations can be made therein without departing from the spirit and scope of the invention as defined by the appended claims.

What is claimed is:

1. A vision inspection system for inspecting a plurality of sides of electronic components, comprising:

an inspection window having a plurality of inspection regions which correspond to various ones of leads of the sides of the components;

an illumination source for directing light to each of said plurality of inspection regions, and illuminating portions of the component which are disposed within said plurality of inspection regions of said inspection window;

optical signals which comprise light from said illumination source which passes into the plurality of inspection regions and illuminate the edges of various ones of the leads of the components;

optical signal directing members for instantaneously directing at least two optical signals of different angular directions from one edge of each of the various ones of the leads disposed in said plurality of inspection regions to preselected points, wherein four of said optical signals are translated on a singular translated frame by said optical translating device;

an optical signal translating device for outputting electrical signals which correspond to said optical signals directed to each of said preselected points; and an optical signal translating device output for providing said electrical signals corresponding to said optical signals to a signal processor for processing to determine the locations of the edges of the various ones of the leads of the component which are disposed in said plurality of inspection regions; and wherein said optical signal directing members comprise reflective surfaces which are mounted for selectively adjusting in conjunction with one another such that said plurality of inspection regions are moveable into one of closer spaced positions and spaced further apart positions such that said vision inspection system accommodates inspection of various sizes of components and said optical signal translating device remains fixably attached within said vision inspection system, set at a singular adjustment for all of said positions of said plurality of inspection regions.

2. The vision inspection system of claim 1, wherein said optical signal translating device comprises two separate cameras, each of which translate multiples ones of said plurality of optical signals onto singular frames.

3. The vision inspection system of claim 1, wherein said illumination source comprises a continuous light source which extends on the side of the leads on which the edges of the leads being located are disposed, such that the optical signals directed to and translated by the optical signal translating device comprise reflected light signals.

4. The vision inspection system of claim 1, wherein said illumination source comprises a flash lamp which is strobed to provide a flash of light for instantaneously translating said various optical signals simultaneously.

5. A vision inspection system for inspecting a plurality of sides of electronic components, comprising:

an inspection window having a plurality of inspection regions which correspond to various ones of leads of the sides of the components;

an illumination source for directing light to each of said plurality of inspection regions and illuminating portions of the component which are disposed within said plurality of inspection regions of said inspection window;

optical signals which comprise light from said illumination source which passes into the plurality of inspection regions and illuminate the edges of various ones of the leads of the components;

optical signal directing members for instantaneously directing at least two optical signals of different angular directions from one edge of each of the various ones of the leads disposed in said plurality of inspection regions to preselected point;

an optical signal translating device for outputting electrical signals which correspond to said optical signals directed to each of said preselected points;

an optical signal translating device output for providing said electrical signals corresponding to said optical signals to a signal processor for processing to determine the locations of the edges of the various ones of the leads of the component which are disposed in said plurality of inspection regions; and wherein said angular directions extend downward and underneath the component and into a central region of side vision system located beneath said inspection window.

6. A vision inspection system for inspecting a plurality of sides of electronic components, comprising:

an inspection window having a plurality of inspection regions which correspond to various ones of leads of the sides of the components;

an illumination source for directing light to each of said plurality of inspection regions, and illuminating portions of the component which are disposed within said plurality of inspection regions of said inspection window;

optical signals which comprise light from said illumination source which passes into the plurality of inspection regions illuminate the edges of various ones of the leads of the components;

optical signal directing members for instantaneously directing at least two optical signals of different angular directions from one edge of each of the various ones of the leads disposed in said plurality of inspection regions to preselected points;

an optical signal translating device for outputting electrical signals which correspond to said optic signals directed to each of said preselected points;

an optical signal translating device output for providing said electrical signals corresponding to said optical signal to a signal processor for processing to determine the locations of the edges of the various ones of the leads of the component which are disposed in said plurality of inspection regions; and wherein said optical signals comprise light which is reflected from the various ones of the leads of the component.

7. A vision inspection system for inspecting a plurality of sides of electronic components, comprising:

an inspection window having a plurality of inspection regions which correspond to various ones of leads of the sides of the components;

an illumination source for directing light to each of said plurality of inspection regions, and illuminating portions of the component which are disposed within said polarity of inspection regions of said inspection window;

optical signals which comprise light from said illumination source which passes into the plurality of inspection regions and illuminate the edges of various ones of the leads of the components;

optical signal directing members for instantaneously directing at least two optical signals of different angular directions from one edge of each of the various ones of the leads disposed in said plurality of inspection regions to preselected points;

an optical signal translating device for outputting electrical signals which correspond to said optical signals directed to each of said preselected points;

an optical signal translating device output for providing said electrical signals corresponding to said optical signals to a signal processor for processing to determine the locations of the edges of the various ones of the leads of the component which are disposed in said plurality of inspection regions;

wherein said illumination source comprises a continuous light source which extends on the side of the leads on which the edges of the leads being located are disposed, such that the optical signals directed to and translated by the optical signal translating device comprise reflected light signals;

a first beam splitter disposed between at least a portion of said optical signal directing members and said plurality of inspection regions of said inspection window; and a second beam splitter disposed between said optical directing members and said illumination source, such that at least a portion of said optical signals which are directed by said optical signal directing members to said optical signal translating device pass through said beam splitter.

8. A vision inspection system for inspecting a plurality of sides of electronic components, comprising:

an inspection window having a plurality of inspection regions which correspond to various ones of leads of the sides of the components;

an illumination source for directing light to each of said plurality of inspection regions, and illuminating portions of the component which are disposed within said plurality of inspection regions of said inspection window;

optical signals which comprise light from said illumination source which passes into the plurality of inspection regions and illuminate the edges of various ones of the leads of the components;

optical signal directing members for instantaneously directing at least two optical signals of different angular directions from one edge of each of the various ones of the leads disposed in said plurality of inspection regions to preselected points;

an optical signal translating device for outputting electrical signals which correspond to said optical signals directed to each of said preselected points;

an optical signal translating device output for providing said electric signals corresponding to said optical signals to a signal processor for processing to determine the locations of the edges of the various ones of the leads of the component which are disposed in said plurality of inspection regions;

a vision inspection system of claim 4, wherein said illumination source comprises a flash lamp which is strobed to provide a flash of light for instantaneously translating said various optical signals simultaneously;

a first beam splitter disposed between at least a portion of said optical signal directing members and said plurality of inspection regions of said inspection window; and a second beam splitter disposed between said optical directing members and said illumination source, such that at least a portion of said optical signals which are directed by said optical signal directing members to said optical signal translating device pass through said beam splitter.

9. A vision inspection system for inspecting a plurality of sides of electronic components, comprising:

an inspection window having a plurality of inspection regions which correspond to various ones of leads of the sides of the components;

an illumination source for directing light to each of said plurality of inspection regions, and illuminating portions of the component which are disposed within said plurality of inspection regions of said inspection window;

optical signals which comprise light from said illumination source which passes into the plurality of inspection regions and illuminate the edges of various ones of the leads of the components;

optical signal directing members for instantaneously directing at least two optical signals of different angular directions from one edge of each of the various ones of the leads disposed in said plurality of inspection regions to preselected points;

an optical signal translating device for outputting electrical signals which correspond to said optical signals directed to each of said preselected points;

an optical signal translating device output for providing said electrical signals corresponding to said optical signals to a signal processor for processing to determine the locations of the edges of the various ones of the leads of the component which are disposed in said plurality of inspection regions;

wherein said optical signal directing members comprise reflective surfaces which are mounted for selectively adjusting in conjunction with one another such that said plurality of inspection regions are moveable into one of a closer spaced positions and spaced further apart positions, such that said vision inspection system accommodates inspection of various sizes of components with said optical signal translating device remaining fixably attached within said vision inspection system, set at a singular adjustment for all of said positions of said plurality of inspection regions;

wherein said plurality of inspection regions comprise at least four regions which are spaced apart on said four sides of an electronic component;

said optical signals comprise at least eight optical signals, two emanating in separate directions from said same side of said portion of the component within each of said respective ones of said plurality of inspection regions such that two signals emanate from each of said four inspection regions;

said angular directions of said optical signals extending downward from and underneath the component, into a central region of said vision inspection system which is disposed beneath said inspection window; and wherein said optical signal translating device comprises two cameras, each translating four of said optical signals from said ones of said inspection regions which are on opposite sides of said components from said other, and each of said cameras translating said optical signals from said inspection regions which are adjacent to those translated by said other camera.

10. A vision inspection system for inspecting a plurality of sides of electronic components, comprising:

an inspection window having a plurality of inspection regions which correspond to various ones of the sides of the components;

an illumination source for directing light to each of said plurality of inspection regions, and illuminating portions of the component which are disposed within said plurality of inspection regions and face said inspection window;

optical signals which comprise light from said illumination source which is reflected from the edges of portions of leads of the component which are disposed within each of said plurality of inspection regions;

optical signal directing members for instantaneously directing at least two optical signals of different angular directions from each of the edges of the leads disposed in said plurality of inspection regions to preselected points;

an optical signal translating device for translating said optical signals directed to each of said preselected points, with multiple ones of said plurality of optical signals translated on a singular translated frame by said optical signal translating device; and an optical signal translating device output for providing a signal corresponding to said frame of said optical signals to a signal processor for processing said output corresponding to said optical signals reflected from the portions of the component which are disposed in said various ones of said plurality of inspection regions to determine the location of the edges of the leads disposed in the plurality of inspection regions.

11. The vision inspection system of claim 10, wherein said angular directions extend downward and underneath the component and into a central region of said vision system located beneath said inspection window.

12. The vision inspection system of claim 10, wherein said optical signal directing members comprise reflective surfaces.

13. The vision inspection system of claim 12, wherein at least a portion of said reflective surfaces are mounted for selectively adjusting in conjunction with one another such that said plurality of inspection regions are moveable into one of a closer spaced positions, and spaced further apart positions, such that said vision inspection system accommodates inspection of various sizes of components and said optical signal translating device remains fixably attached within said vision inspection system, set at a singular adjustment for all of said positions of said plurality of inspection regions.

14. The vision inspection system of claim 10, wherein said illumination source comprises a continuous light source which extends adjacent to and around one end of said inspection window in a spaced apart relation thereto.

15. The vision inspection system of claim 14, and further comprising:

a first beam splitter disposed between at least a portion of said optical signal directing members and said plurality of inspection regions of said inspection window; and a second beam splitter disposed between said optical directing members and said illumination source, such that at least a portion of said optical signals which are directed by said optical signal directing members to said optical signal translating device pass through said beam splitter.

16. The vision inspection system of claim 10, wherein said illumination source is a flash lamp which is strobed to provide a flash of light for instantaneously translating said various optical signals simultaneously.

17. The vision inspection system of claim 16, and further comprising:

a first beam splitter disposed between at least a portion of said optical signal directing members and said plurality of inspection regions of said inspection window; and a second beam splitter disposed between said optical directing members and said illumination source, such that at least a portion of said optical signals which are directed by said optical signal directing members to said optical signal translating device pass through said beam splitter.

18. The vision inspection system of claim 10, wherein said optical signal directing members comprise reflective surfaces which are mounted for selectively adjusting in conjunction with one another such that said plurality of inspection regions are moveable into one of a closer spaced position, and spaced further apart positions, such that said vision inspection system accommodates inspection of various sizes of components with said optical signal translating device remaining fixably attached within said vision inspection system, set at a singular adjustment for all of said positions of said plurality of inspection regions;

wherein said plurality of inspection regions comprise at least four regions which are spaced apart on said four sides of an electronic component;

said optical signals comprise at least eight optical signals, two emanating in separate directions from said same side of said portion of the component within each of said respective ones of said plurality of inspection regions such that two signals emanate from each of said four inspection regions;

said angular directions of said optical signals extending downward from and underneath the component, into a central region of said vision inspection system which is disposed beneath said inspection window; and wherein said optical signal translating device comprises two cameras, each translating four of said optical signals from said ones of said inspection regions which are on opposite sides of said components from said other, and each of said cameras translating said optical signals from said inspection regions which are adjacent to those translated by said other camera.

19. The vision inspection system of claim 10, wherein said optical signal translating device comprises two separate cameras, each of which translate multiples ones of said plurality of optical signals onto singular frames.

* * * * *

UNITED STATES PATENT AND TRADEMARK OFFICE
CERTIFICATE OF CORRECTION

PATENT NO. : 5,910,844
DATED : June 8, 1999
INVENTOR(S) : Dennis D. phillips and Brian H. Jones It is certified that error appears in the above-indentified patent and that said Letters Patent is hereby corrected as shown below:

Column 9, line 29, delete "side", insert thereof --said--;

Column 11, line 1, Claim 8, delete "4", insert thereof --6--.

Signed and Sealed this

Tenth Day of April, 2001

*Attest:*

NICHOLAS P. GODICI

*Attesting Officer*     *Acting Director of the United States Patent and Trademark Office*